(12) United States Patent
Nakazawa

(10) Patent No.: US 8,258,349 B2
(45) Date of Patent: Sep. 4, 2012

(54) PROCESS FOR PRODUCTION OF BENZALDEHYDE COMPOUND

(75) Inventor: Koichi Nakazawa, Toyonaka (JP)

(73) Assignee: Suitomo Chemical Company, Limited, Tokyo (JP)

( * ) Notice: Subject to any disclaimer, the term of this patent is extended or adjusted under 35 U.S.C. 154(b) by 230 days.

(21) Appl. No.: 12/863,759

(22) PCT Filed: Jan. 30, 2009

(86) PCT No.: PCT/JP2009/052014
§ 371 (c)(1),
(2), (4) Date: Jul. 20, 2010

(87) PCT Pub. No.: WO2009/101898
PCT Pub. Date: Aug. 20, 2009

(65) Prior Publication Data
US 2010/0292513 A1    Nov. 18, 2010

(30) Foreign Application Priority Data
Feb. 14, 2008   (JP) .................. 2008-032763

(51) Int. Cl.
C07C 45/00 (2006.01)
C07C 43/30 (2006.01)
(52) U.S. Cl. .......... 568/425; 568/437; 568/592
(58) Field of Classification Search .......... 568/425, 568/437, 592
See application file for complete search history.

(56) References Cited

U.S. PATENT DOCUMENTS

| | | | |
|---|---|---|---|
| 4,748,257 A * | 5/1988 | Fuchs et al. | 549/453 |
| 4,845,249 A * | 7/1989 | Fuchs et al. | 549/455 |
| 5,145,980 A | 9/1992 | Wenderoth et al. | |
| 5,178,662 A * | 1/1993 | Ishii et al. | 504/243 |
| 2010/0210879 A1 | 8/2010 | Nakazawa | |
| 2010/0234645 A1 | 9/2010 | Nakazawa | |

FOREIGN PATENT DOCUMENTS

| | | |
|---|---|---|
| JP | 52-23075 A | 2/1977 |
| JP | 64-83039 A | 3/1989 |
| JP | 1-228931 A | 9/1989 |
| JP | 9-95462 A | 4/1997 |

OTHER PUBLICATIONS

Translated by Kiyoshi Tomioka, "Yuki Gosei no Senryaku—Gyaku Gosei no Know-how," 1st edition, 1st print, issued by Kagaku-Doujin Publishing Co., Inc., 1998, pp. 36 and 37, including a partial English translation of Chapter b only (on p. 37).

English translation of International Preliminary Report on Patentability (Form PCT/IB/338 and 373) and of Written Opinion of the International Searching Authority (Form PCT/ISA/237) mailed Oct. 14, 2010 in international Application No. PCT/JP2009/052014.

* cited by examiner

*Primary Examiner* — Sikarl Witherspoon
(74) *Attorney, Agent, or Firm* — Birch, Stewart, Kolasch & Birch, LLP

(57) ABSTRACT

A benzaldehyde acetal compound of formula (3):

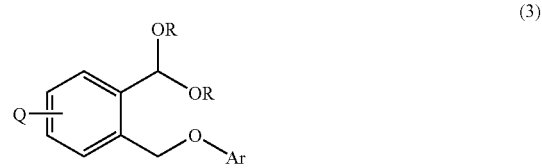

(3)

(wherein Q represents a hydrogen atom or a halogen atom, Ar represents a phenyl group optionally substituted with at least one selected from the group consisting of alkyl groups having 1 to 4 carbon atoms and halogen atoms, and R represents an alkyl group having 1 to 4 carbon atoms).

23 Claims, No Drawings

PROCESS FOR PRODUCTION OF BENZALDEHYDE COMPOUND

TECHNICAL FIELD

The present invention relates to a method for producing a benzaldehyde compound.

BACKGROUND ART

A benzaldehyde compound of formula (4):

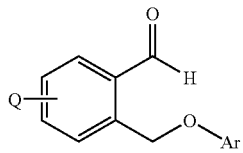

(4)

(wherein Q represents a hydrogen atom or a halogen atom, and Ar represents a phenyl group optionally substituted with at least one selected from the group consisting of alkyl groups having 1 to 4 carbon atoms and halogen atoms.)
is useful as a production intermediate of a disinfectant (see, e.g., JP-A No. 9-95462 and U.S. Pat. No. 5,145,980).

Regarding a method for producing a benzaldehyde compound of formula (4), JP-A No. 9-95462 discloses a method of oxidizing a corresponding benzyl halide compound and U.S. Pat. No. 5,245,980 discloses a method of oxidizing a corresponding benzonitrile compound.

DISCLOSURE OF THE INVENTION

The present invention provides the followings.

<1> A benzaldehyde acetal compound of formula (3):

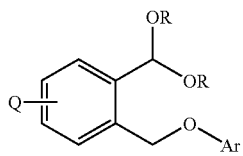

(3)

(wherein, Q represents a hydrogen atom or a halogen atom, Ar represents a phenyl group optionally substituted with at least one selected from the group consisting of alkyl groups having 1 to 4 carbon atoms and halogen atoms, and R represents an alkyl group having 1 to 4 carbon atoms);

<2> The benzaldehyde acetal compound according to <1>, wherein R is a methyl group;

<3> The benzaldehyde acetal compound according to <1> or <2>, wherein Ar is a phenyl group substituted with at least one alkyl group having 1 to 4 carbon atoms;

<4> The benzaldehyde acetal compound according to <3>, wherein the phenyl group substituted with at least one alkyl group having 1 to 4 carbon atoms is 2,5-dimethylphenyl group;

<5> The benzaldehyde acetal compound according to <1>, wherein R represents a methyl group, Ar represents 2,5-dimethylphenyl group and Q represents a hydrogen atom;

<6> A method for producing a benzaldehyde compound, which comprises recting a benzaldehyde acetal compound of formula (3):

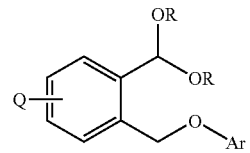

(3)

(wherein Q and Ar respectively represent the same meanings as described below)
with water in the presence of an acid to produce a benzaldehyde compound of formula (4):

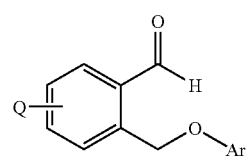

(4)

(wherein Q represents a hydrogen atom or a halogen atom, Ar represents a phenyl group optionally substituted with at least one selected from the group consisting of alkyl groups having 1 to 4 carbon atoms and halogen atoms, and R represents an alkyl group having 1 to 4 carbon atoms);

<7> The method for producing a benzaldehyde compound according to <6>, wherein the acid is a Broensted acid;

<8> The method for producing a benzaldehyde compound according to <7>, wherein the Broensted acid is a sulfuric acid;

<9> A method for producing a benzaldehyde dialkylacetal compound of formula (3):

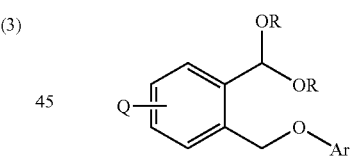

(3)

(wherein Q, Ar and R respectively represent the same meanings as described below),
which comprises reacting a benzal halide compound of formula (1):

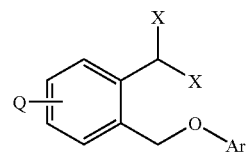

(1)

(wherein Q represents a hydrogen atom or a halogen atom, X represents a halogen atom and Ar represents a phenyl group optionally substituted with at least one selected from the group consisting of alkyl groups having 1 to 4 carbon atoms and halogen atoms)

with an alkali metal alkoxide of formula (2):

(2)

(wherein, R represents an alkyl group having 1 to 4 carbon atoms and M represents an alkali metal atom);

<10> The method for producing a benzaldehyde dialkylacetal compound according to <9>, wherein the benzal halide compound of formula (1) and the alkali metal alkoxide of formula (2) are reacted in the presence of iodine or an iodine compound;

<11> The method for producing a benzaldehyde dialkylacetal compound according to <10>, wherein the iodine compound is an alkali metal iodide;

<12> The method for producing a benzaldehyde dialkylacetal compound according to any one of <9> to <11>, wherein the benzal halide compound of formula (1) and the alkali metal alkoxide of formula (2) are reacted in the presence of a phase transfer catalyst;

<13> The method for producing a benzaldehyde dialkylacetal compound according to <12>, wherein the phase transfer catalyst is a quaternary ammonium salt;

<14> A benzal halide compound of formula (1):

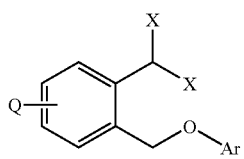
(1)

(wherein, Q represents a hydrogen atom or a halogen atom, X represents a halogen atom and Ar represents a phenyl group optionally substituted with at least one selected from the group consisting of alkyl groups having 1 to 4 carbon atoms and halogen atoms);

<15> The benzal halide compound according to <14>, wherein the halogen atom is a chlorine atom;

<16> The benzal halide compound according to <14> or <15>, wherein Ar is a phenyl group substituted with at least one alkyl group having 1 to 4 carbon atoms;

<17> The benzal halide compound according to <16>, wherein the phenyl group substituted with at least one alkyl group having 1 to 4 carbon atoms is 2,5-dimethylphenyl group;

<18> The benzal halide compound according to <14>, wherein X is a chlorine atom, Ar is 2,5-dimethylphenyl group and Q is a hydrogen atom;

<19> A method for producing a benzal halide compound of formula (1):

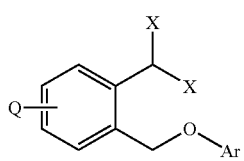
(1)

(wherein Q, X and Ar respectively represent the same meanings as described below),
which comprises reacting a benzal halide compound of formula (5):

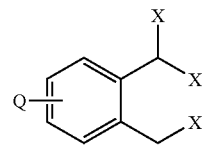
(5)

(wherein Q and X respectively represent the same meanings as described above)
with a phenol compound of formula (6):

(6)

(wherein Ar represents the same meaning as described above)
in the presence of a base;

<20> The method for producing a benzal halide compound according to <19>, wherein a mixture of the phenol compound of formula (6) with the base is added to a benzal halide compound of formula (5) to perform a reaction thereof;

<21> The method for producing a benzal halide compound according to <19> or <20>, wherein a benzal halide compound of formula (5) and a phenol compound of formula (6) are reacted in the presence of a phase transfer catalyst;

<22> A method for producing a benzaldehyde compound, which comprises (A) a step of reacting a benzal halide compound of formula (1):

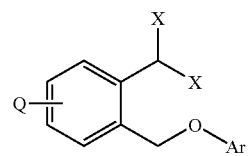
(1)

(wherein Q represents a hydrogen atom or a halogen atom, X represents a halogen atom and Ar represents a phenyl group optionally substituted with at least one selected from the group consisting of alkyl groups having 1 to 4 carbon atoms and halogen atoms) with an alkali metal alkoxide of formula (2):

(2)

(wherein R represents an alkyl group having 1 to 4 carbon atoms and M represents an alkali metal atom)
to give a benzaldehyde dialkylacetal compound of formula (3):

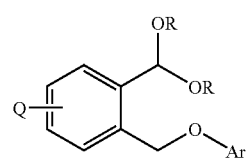
(3)

(wherein Q, Ar and R respectively represent the same meanings as described above), and (B) a step of reacting the benzaldehyde dialkylacetal compound of formula (3) with water in the presence of an acid to give a benzaldehyde compound of formula (4):

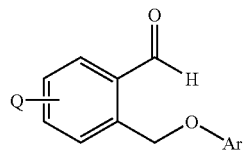

(4)

(wherein Q and Ar respectively represent the same meanings as described above); and <23> The method for producing a benzaldehyde compound according to <22>, further comprising (C) a step of reacting a benzal halide compound of formula (5):

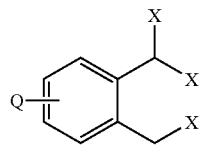

(5)

(wherein Q and X respectively represent the same meanings as described above)
with a phenol compound of formula (6):

Ar—OH (6)

(wherein Ar represents the same meaning as described above) in the presence of a base to give the benzal halide compound of formula (1):

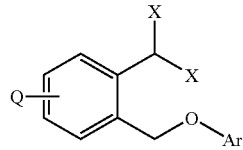

(1)

(wherein Q, X and Ar respectively represent the same meanings as described above).

BEST MODES FOR CARRYING OUT THE INVENTION

First, a benzaldehyde acetal compound of formula (3):

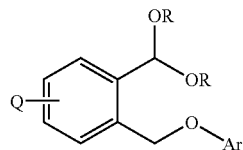

(3)

(wherein, Q represents a hydrogen atom or a halogen atom, Ar represents a phenyl group optionally substituted with at least one selected from the group consisting of alkyl groups having 1 to 4 carbon atoms and halogen atoms, and R represents an alkyl group having 1 to 4 carbon atoms) (hereinafter briefly referred to as acetal compound (3)) will be explained.

In the formula of the acetal compound (3), Q represents a hydrogen atom or a halogen atom, preferably a hydrogen atom. The halogen atom includes a fluorine atom, chlorine atom, bromine atom and iodine atom.

In the formula of the acetal compound (3), Ar represents a phenyl group optionally substituted with at least one selected from the group consisting of alkyl groups having 1 to 4 carbon atoms and halogen atoms. The alkyl group having 1 to 4 carbon atoms include a methyl group, ethyl group, propyl group, isopropyl group, butyl group, isobutyl group, tert-butyl group and the like, and the halogen atom includes a fluorine atom and chlorine atom.

Such a phenyl group optionally substituted with at least one selected from the group consisting of alkyl groups having 1 to 4 carbon atoms and halogen atoms includes a phenyl group, 2-methylphenyl group, 4-methylphenyl group, 5-methylphenyl group, 2,5-dimethylphenyl group, 2,4-dimethylphenyl group, 2,6-dimethylphenyl group, 2,4,6-trimethylphenyl group, 2-ethylphenyl group, 4-ethylphenyl group, 5-ethylphenyl group, 2,5-diethylphenyl group, 2,4-diethylphenyl group, 2,6-diethylphenyl group, 2,4,6-triethylphenyl group, 2-propylphenyl group, 4-propylphenyl group, 5-propylphenyl group, 2,5-dipropylphenyl group, 2,4-dipropylphenyl group, 2,6-dipropylphenyl group, 2,4,6-tripropylphenyl group, 2-isopropylphenyl group, 4-isopropylphenyl group, 5-isopropylphenyl group, 2,5-diisopropylphenyl group, 2,4-diisopropylphenyl group, 2,6-diisopropylphenyl group, 2,4,6-triisopropylphenyl group, 2-butylphenyl group, 4-butylphenyl group, 5-butylphenyl group, 2,5-dibutylphenyl group, 2,4-dibutylphenyl group, 2,6-dibutylphenyl group, 2,4,6-tributylphenyl group, 2-isobutylphenyl group, 4-isobutylphenyl group, 5-isobutylphenyl group, 2,5-diisobutylphenyl group, 2,4-diisobutylphenyl group, 2,6-diisobutylphenyl group, 2,4,6-triisobutylphenyl group, 2-tert-butylphenyl group, 4-tert-butylphenyl group, 5-tert-butylphenyl group, 2,5-di-tert-butylphenyl group, 2,4-di-tert-butylphenyl group, 2,6-di-tert-butylphenyl group, 2,4,6-tri-tert-butylphenyl group, 2-fluorophenyl group, 4-fluorophenyl group, 2,4-difluorophenyl group, 2,4,6-trifluorophenyl group, pentafluorophenyl group, 2-chlorophenyl group, 4-chlorophenyl group, 2,4-dichlorophenyl group, 2,4,6-trichlorophenyl group and pentachlorophenyl group. Among them, phenyl groups substituted with at least one alkyl group having 1 to 4 carbon atoms are preferable, and 2,5-dimethylphenyl group is more preferable.

The acetal compound (3) is a novel compound, and specific examples thereof include
2-(phenoxymethyl)benzaldehyde dimethyl acetal,
2-(2-methylphenoxymethyl)benzaldehyde dimethyl acetal,
2-(2-ethylphenoxymethyl)benzaldehyde dimethyl acetal,
2-(2-isopropylphenoxymethyl)benzaldehyde dimethyl acetal, 2-(4-methylphenoxymethyl)benzaldehyde dimethyl acetal, 2-(4-isopropylphenoxymethyl)benzaldehyde dimethyl acetal,
2-(2,5-dimethylphenoxymethyl)benzaldehyde dimethyl acetal, 2-(2,5-diethylphenoxymethyl)benzaldehyde dimethyl acetal,
2-(2,5-diisopropylphenoxymethyl)benzaldehyde dimethyl acetal, 2-(2,4,5-trimethylphenoxymethyl)benzaldehyde dimethyl acetal,
2-(2,4,6-trimethylphenoxymethyl)benzaldehyde dimethyl acetal, 2-(3,4,5-trimethylphenoxymethyl)benzaldehyde dimethyl acetal, 2-(2,4,5-trimethylphenoxymethyl)benzaldehyde dimethyl acetal,
2-(2,5-dimethylphenoxymethyl)-3-chlorobenzaldehyde dimethyl acetal,
2-(2,5-dimethylphenoxymethyl)-4-chlorobenzaldehyde dimethyl acetal,
2-(2,5-dimethylphenoxymethyl)-5-chlorobenzaldehyde dimethyl acetal,
2-(2,5-dimethylphenoxymethyl)-6-chlorobenzaldehyde dimethyl acetal,
2-(2,5-diethylphenoxymethyl)-3-chlorobenzaldehyde dimethyl acetal,
2-(2,5-diethylphenoxymethyl)-4-chlorobenzaldehyde dimethyl acetal,
2-(2,5-diethylphenoxymethyl)-5-chlorobenzaldehyde dimethyl acetal,
2-(2,5-diethylphenoxymethyl)-6-chlorobenzaldehyde dimethyl acetal,
2-(2,5-diisopropylphenoxymethyl)-3-chlorobenzaldehyde dimethyl acetal,
2-(2,5-diisopropylphenoxymethyl)-4-chlorobenzaldehyde dimethyl acetal,
2-(2,5-diisopropylphenoxymethyl)-5-chlorobenzaldehyde dimethyl acetal,
2-(2,5-diisopropylphenoxymethyl)-6-chlorobenzaldehyde dimethyl acetal,
2-(2,5-dimethylphenoxymethyl)-4-bromobenzaldehyde dimethyl acetal,
2-(2,5-diethylphenoxymethyl)-4-bromobenzaldehyde dimethyl acetal,
2-(2,5-diisopropylphenoxymethyl)-4-bromobenzaldehyde dimethyl acetal,
2-(2,5-dimethylphenoxymethyl)-4-iodobenzaldehyde dimethyl acetal,
2-(2,5-dimethylphenoxymethyl)benzaldehyde diethyl acetal, 2-(2,5-dimethylphenoxymethyl)benzaldehyde dipropyl acetal,
2-(2,5-dimethylphenoxymethyl)benzaldehyde dibutyl acetal, 2-(2,5-dimethylphenoxymethyl)benzaldehyde diisopropyl acetal,
2-(2,5-dimethylphenoxymethyl)benzaldehyde diisobutyl acetal and 2-(2,5-dimethylphenoxymethyl)benzaldehyde di-tert-butyl acetal.

Such an acetal compound (3) and water can be reacted in the presence of an acid to give a benzaldehyde compound of formula (4) (hereinafter, briefly referred to as benzaldehyde compound (4)):

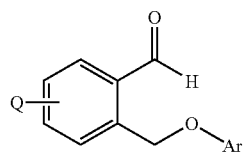

(4)

(wherein Q and Ar respectively represent the same meanings as described above).

The acid includes Broensted acids such as hydrochloric acid, sulfuric acid and nitric acid, and sulfuric acid is preferable. As such acids, commercially available acids are usually used. If necessary, these acids may be diluted with water or solvents described later. The acid is used usually in the form of an aqueous solution.

The use amount of the acid is usually 0.01 mol or more, preferably 1 to 5 mol with respect to 1 mol of acetal compound (3).

The use amount of water is usually 2 mol or more with respect to 1 mol of acetal compound (3), and there is no limitation thereof, and water may be used in large amount also as a solvent simultaneously.

The reaction of acetal compound (3) with water is carried out usually in the presence of an organic solvent. The organic solvent includes aromatic hydrocarbon solvents such as xylene, toluene and benzene; aliphatic hydrocarbon solvents such as pentane, hexane, heptane and cyclohexane; ether solvents such as diethyl ether, tert-butyl methyl ether and cyclopentyl methyl ether; alcohol solvents such as methanol, ethanol, butanol, isopropanol, isobutanol and tert-butanol; and aromatic hydrocarbon solvents are preferable and xylene and toluene are more preferable. Though the use amount of the organic solvent is not restricted, it is usually 100 parts by weight or less with respect to 1 part by weight of acetal compound (3) from the standpoint of volumetric efficiency.

The reaction temperature is usually 1° C. or more and not higher than the boiling point of a solvent, preferably 10 to 100° C.

The reaction may be carried out at normal pressure, or carried out under increased pressure.

The progress of the reaction can be confirmed by usual analysis means such as gas chromatography, high performance liquid chromatography and NMR.

The reaction is carried out by mixing an acid, acetal compound (3) and water, and the mixing order thereof is not restricted, and it is preferable to add an aqueous solution of the acid to acetal compound (3) adjusted to the reaction temperature.

Thus, a reaction mixture containing benzaldehyde compound (4) is obtained, and benzaldehyde compound (4) can be separated out by, for example, concentrating the reaction mixture as it is or washing the reaction mixture before concentration. Benzaldehyde compound (4) separated out may be further purified by usual purification means such as recrystallization, distillation and column chromatography.

Thus obtainable benzaldehyde compound (4) includes
2-(phenoxymethyl)benzaldehyde,
2-(2-methylphenoxymethyl)benzaldehyde,
2-(2-ethylphenoxymethyl)benzaldehyde,
2-(2-isopropylphenoxymethyl)benzaldehyde,
2-(4-methylphenoxymethyl)benzaldehyde,
2-(4-isopropylphenoxymethyl)benzaldehyde,
2-(2,5-dimethylphenoxymethyl)benzaldehyde,
2-(2,5-diethylphenoxymethyl)benzaldehyde,
2-(2,5-diisopropylphenoxymethyl)benzaldehyde,
2-(2,4,5-trimethylphenoxymethyl)benzaldehyde,
2-(2,4,6-trimethylphenoxymethyl)benzaldehyde,
2-(3,4,5-trimethylphenoxymethyl)benzaldehyde,
2-(2,4,5-trimethylphenoxymethyl)benzaldehyde,
2-(2,5-dimethylphenoxymethyl)-3-chlorobenzaldehyde,
2-(2,5-dimethylphenoxymethyl)-4-chlorobenzaldehyde,
2-(2,5-dimethylphenoxymethyl)-5-chlorobenzaldehyde,
2-(2,5-dimethylphenoxymethyl)-6-chlorobenzaldehyde,
2-(2,5-diethylphenoxymethyl)-3-chlorobenzaldehyde,
2-(2,5-diethylphenoxymethyl)-4-chlorobenzaldehyde,
2-(2,5-diethylphenoxymethyl)-5-chlorobenzaldehyde,
2-(2,5-diethylphenoxymethyl)-6-chlorobenzaldehyde,
2-(2,5-diisopropylphenoxymethyl)-3-chlorobenzaldehyde,
2-(2,5-diisopropylphenoxymethyl)-4-chlorobenzaldehyde,
2-(2,5-diisopropylphenoxymethyl)-5-chlorobenzaldehyde,
2-(2,5-diisopropylphenoxymethyl)-6-chlorobenzaldehyde,
2-(2,5-dimethylphenoxymethyl)-4-bromobenzaldehyde,
2-(2,5-diethylphenoxymethyl)-4-bromobenzaldehyde,
2-(2,5-diisopropylphenoxymethyl)-4-bromobenzaldehyde and 2-(2,5-dimethylphenoxymethyl)-4-iodobenzaldehyde.

Acetal compound (3) can be produced by reacting a benzal halide compound of formula (1) (hereinafter, briefly referred to as benzal halide compound (1)):

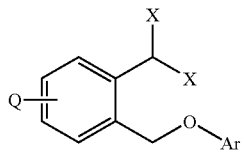

(wherein Q and Ar respectively represent the same meanings as described above, and X represents a halogen atom) with an alkali metal alkoxide of formula (2) (hereinafter, briefly referred to as alkali metal alkoxide (2)):

RO—M    (2)

(wherein R represents the same meaning as described above, and M represents an alkali metal atom).

In the formula of benzal halide compound (1), X represents a halogen atom, and the halogen atom includes a chlorine atom, bromine atom and iodine atom, preferably a chlorine atom.

Also benzal halide compound (1) is a novel compound, and specific examples thereof include
2-(phenoxymethyl)benzal chloride,
2-(2-methylphenoxymethyl)benzal chloride,
2-(2-ethylphenoxymethyl)benzal chloride,
2-(2-isopropylphenoxymethyl)benzal chloride,
2-(4-methylphenoxymethyl)benzal chloride,
2-(4-isopropylphenoxymethyl)benzal chloride,
2-(2,5-dimethylphenoxymethyl)benzal chloride,
2-(2,5-diethylphenoxymethyl)benzal chloride,
2-(2,5-diisopropylphenoxymethyl)benzal chloride,
2-(2,4,5-trimethylphenoxymethyl)benzal chloride,
2-(2,4,6-trimethylphenoxymethyl)benzal chloride,
2-(3,4,5-trimethylphenoxymethyl)benzal chloride,
2-(2,4,5-trimethylphenoxymethyl)benzal chloride,
2-(2,5-dimethylphenoxymethyl)-3-chlorobenzal chloride,
2-(2,5-dimethylphenoxymethyl)-4-chlorobenzal chloride,
2-(2,5-dimethylphenoxymethyl)-5-chlorobenzal chloride,
2-(2,5-dimethylphenoxymethyl)-6-chlorobenzal chloride,
2-(2,5-diethylphenoxymethyl)-3-chlorobenzal chloride,
2-(2,5-diethylphenoxymethyl)-4-chlorobenzal chloride,
2-(2,5-diethylphenoxymethyl)-5-chlorobenzal chloride,
2-(2,5-diethylphenoxymethyl)-6-chlorobenzal chloride,
2-(2,5-diisopropylphenoxymethyl)-3-chlorobenzal chloride,
2-(2,5-diisopropylphenoxymethyl)-4-chlorobenzal chloride,
2-(2,5-diisopropylphenoxymethyl)-5-chlorobenzal chloride,
2-(2,5-diisopropylphenoxymethyl)-6-chlorobenzal chloride,
  2-(2,5-diethylphenoxymethyl)benzal bromide,
2-(2,5-diethylphenoxymethyl)benzal iodide,
2-(2,5-dimethylphenoxymethyl)-4-bromobenzal bromide,
  2-(2,5-diethylphenoxymethyl)-4-bromobenzal bromide,
2-(2,5-diisopropylphenoxymethyl)-4-bromobenzal bromide
  and 2-(2,5-dimethylphenoxymethyl)-4-iodobenzal iodide.

In the formula of alkali metal alkoxide (2), M represents an alkali metal atom, and the alkali metal atom includes a lithium atom, sodium atom, potassium atom, rubidium atom, cesium atom and francium atom, preferably a sodium atom.

Alkali metal alkoxide (2) includes lithium alkoxides such as lithium methoxide, lithium ethoxide, lithium propoxide, lithium butoxide, lithium isopropoxide, lithium isobutoxide, and lithium tert-butoxide; sodium alkoxides such as sodium methoxide, sodium ethoxide, sodium propoxide, sodium butoxide, sodium isopropoxide, sodium isobutoxide and sodium tert-butoxide; potassium alkoxides such as potassium methoxide, potassium ethoxide, potassium propoxide, potassium butoxide, potassium isopropoxide, potassium isobutoxide and potassium tert-butoxide; rubidium alkoxides such as rubidium methoxide, rubidium ethoxide, rubidium propoxide, rubidium butoxide, rubidium isopropoxide, rubidium isobutoxide and rubidium tert-butoxide; cesium alkoxides such as cesium methoxide, cesium ethoxide, cesium propoxide, cesium butoxide, cesium isopropoxide, cesium isobutoxide and cesium tert-butoxide; francium alkoxides such as francium methoxide, francium ethoxide, francium propoxide, francium butoxide, francium isopropoxide, francium isobutoxide and francium tert-butoxide. Among them, sodium alkoxides are preferable and sodium methoxide is more preferable.

As alkali metal alkoxide (2), commercially available compounds may be used, and those prepared by reacting a corresponding alcohol and a corresponding alkali metal hydride or alkali metal hydroxide may also be used. Further, preparation of alkali metal alkoxide (2) and reaction of benzal halide compound (1) anwithd alkali metal alkoxide (2) may be carried out simultaneously by mixing benzal halide compound (1) and a corresponding alcohol and a corresponding alkali metal hydride or alkali metal hydroxide.

Though the use amount of the alkali metal alkoxide (2) is not restricted, it is usually 2 to 10 mol, preferably 3 to 5 mol with respect to 1 mol of benzal halide compound (1).

Reaction of benzal halide compound (1) and alkali metal alkoxide (2) may be carried out in the presence of a solvent, or may be carried out in the absence of a solvent. It is preferable to perform the reaction in the presence of a solvent.

The solvent includes aromatic hydrocarbon solvents such as xylene, toluene and benzene; aliphatic hydrocarbon solvents such as pentane, hexane, heptane and cyclohexane; ether solvents such as tetrahydrofuran, diethyl ether, tert-butylmethyl ether and cyclopentylmethyl ether; alcohol solvents such as methanol, ethanol, butanol, isopropanol, isobutanol and tert-butanol. Among them, alcohol solvents are preferable, and alcohols solvents having the same alkoxy group as that of alkali metal alkoxide (2) to be used are more preferable.

Though the use amount of a solvent is not restricted, it is usually 100 parts by weight or less with respect to 1 part by weight of benzal halide compound (1) from the standpoint of economy.

By carrying out a reaction of benzal halide compound (1) with alkali metal alkoxide (2) in the presence of a phase transfer catalyst, the reaction can be progressed smoothly.

The phase transfer catalyst includes quaternary ammonium salts such as tetra n-butylammonium bromide, benzyltriethylammonium chloride, tetra n-butylammonium hydrogen sulfate and trioctylmethylammonium chloride; phosphonium salts such as triphenylphosphine bromide; polyether compounds such as 18-crown-6 and polyethylene glycol. Among them, quaternary ammonium salts are preferable, and tetra n-butylammonium bromide is more preferable As the phase transfer catalyst, commercially available compounds are usually used.

The use amount of the phase transfer catalyst is usually 0.01 mol or more, preferably 0.05 to 1 mol with respect to 1 mol of benzal halide compound (1).

Further, also by carrying out a reaction of benzal halide compound (1) and alkali metal alkoxide (2) in the presence of iodine or an iodine compound, the reaction can be progressed smoothly.

The iodine compound includes alkali metal iodides such as potassium iodide, sodium iodide and lithium iodide; etc., and alkali metal iodides are preferable and potassium iodide is more preferable. As the iodine and the iodine compound, commercially available compounds are usually used.

The use amount of iodine or an iodine compound is usually 0.01 mol or more, preferably 0.05 to 1 mol with respect to 1 mol of benzal halide compound (1).

The reaction temperature is usually −5° C. or more and not higher than the boiling point of a solvent, and preferably 10 to 100° C.

The reaction is carried out by mixing benzal halide compound (1) with alkali metal alkoxide (2). Though the mixing order thereof is not restricted, it is preferable to add alkali metal alkoxide (2) to benzal halide compound (1) adjusted to the reaction temperature.

The reaction may be carried out at normal pressure, or carried out under increased pressure.

The progress of the reaction can be confirmed by usual analysis means such as gas chromatography, high performance liquid chromatography and NMR.

Thus, a reaction mixture containing acetal compound (3) is obtained, and acetal compound (3) can be separated out by concentrating the reaction mixture as it is or washing the reaction mixture before concentration. The acetal compound (3) separated out may be further purified by usual purification means such as recrystallization, distillation and column chromatography.

Further, the reaction mixture may be used as it is for reaction with water in the presence of the above-described acid, or the reaction mixture may be washed with water to remove alkali metal alkoxides and the like remaining in the reaction mixture, and used for reaction with water in the presence of the acid. In the case of washing of the reaction mixture with water, if necessary, organic solvents insoluble in water such as aromatic hydrocarbon solvents such as xylene, toluene and benzene; aliphatic hydrocarbon solvents such as pentane, hexane, heptane and cyclohexane may be added.

A benzal halide compound (1) can be produced by reacting a benzal halide compound of formula (5) (hereinafter, briefly referred to as benzal halide compound (5)):

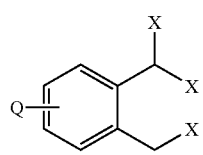

(5)

(wherein Q and X respectively represent the same meanings as described above)
with a phenol compound of formula (6) (hereinafter, referred to as phenol compound (6)):

Ar—OH (6)

(wherein Ar represents the same meaning as described above) in the presence of a base.

The benzal halide compound (5) includes 2-(chloromethyl)benzal chloride, 2-(bromomethyl)benzal bromide, 2-(iodomethyl)benzal iodide, 3-chloro-2-(chloromethyl)benzal chloride, 4-chloro-2-(chloromethyl)benzal chloride, 4-bromo-(bromomethyl)benzal bromide, 4-iodo-2-(iodomethyl)benzal iodide, 5-chloro-2-(chloromethyl)benzal chloride, 5-bromo-(bromomethyl)benzal bromide, 5-iodo-2-(iodomethyl)benzal iodide, 6-chloro-2-(chloromethyl)benzal chloride and the like, and preferable from the standpoint of availability is 2-(chloromethyl)benzal chloride.

As benzal halide compound (5) commercially available compounds may be used, and those produced according to known methods such as a method of reacting an o-xylene compound and a halogen in the presence of a radical initiator or under light illumination (see, JP-A No. 2006-335737), and the like, may be used.

Phenol compound (6) includes phenol, 2-methylphenol, 2-ethylphenol, 2-isopropylphenol, 4-methylphenol, 4-isopropylphenol, 2,5-dimethylphenol, 2,5-diethylphenol, 2,5-diisopropylphenol, 2,4,5-trimethylphenol, 2,4,6-trimethylphenol, 3,4,5-trimethylphenol, 2-chlorophenol, 4-chlorophenol, 2-fluorophenol, 4-fluorophenol, 2,4-difluorophenol, 2,4,6-trifluorophenol and the like, and 2,5-dimethylphenol is preferable.

As phenol compound (6), commercially available compounds may be used, and those produced by known methods described in J. Am. Chem. Soc., 128, 10694 (2006), Tetrahedron Letters, 30, 5215 (1989), JP-A No. 2002-3426 and the like, may be used.

An excess amount of phenol compound (6) may be used with respect to benzal halide compound (5), alternatively an excess amount of benzal halide compound (5) maybe used with respect to phenol compound (6). Phenol compound (6) is used in an amount of preferably 0.1 to 10 mol, more preferably 1 to 3 mol with respect to 1 mol of benzal halide compound (5).

The base includes tertiary amines such as trimethylamine, triethylamine and diisopropylethylamine; alkali metal alkoxides such as sodium methoxide, sodium ethoxide and potassium tert-butoxide; alkali metal hydroxides such as lithium hydroxide, sodium hydroxide and potassium hydroxide; alkali metal hydride compounds such as sodium hydride, potassium hydride and lithium hydride; alkali metal carbonates such as sodium carbonate, potassium carbonate and lithium carbonate; alkali metal hydrogen carbonates such as sodium hydrogen carbonate, potassium hydrogen carbonate and lithium hydrogen carbonate. Among them, alkali metal hydroxides are preferable, and sodium hydroxide is more preferable. As the base, commercially available compounds are usually used as they are. Further, the base may be diluted with water or solvents to be described later.

The use amount of the base is usually 1 mol or more with respect to 1 mol of the compound which is used in the smaller amount of benzal halide compound (5) and phenol compound (6). Though there is no limitation on the use amount, it is preferably 1 to 3 mol.

The reaction of benzal halide compound (5) with phenol compound (6) is usually carried out in the presence of a solvent. The solvent includes aromatic hydrocarbon solvents such as xylene, toluene and benzene; aliphatic hydrocarbon solvents such as pentane, hexane, heptane and cyclohexane; ether solvents such as tetrahydrofuran, diethyl ether, tert-butylmethyl ether and cyclopentylmethyl ether; nitrile solvents such as acetonitrile and propionitrile; ketone solvents such as tert-butyl methyl ketone; amide solvents such as N,N-dimethylformamide; sulfoxide solvents such as dimethyl sulfoxide; and water. Particularly, mixed solvents composed of water and aromatic hydrocarbon solvents are preferable, and a mixed solvent of water and toluene is more preferable. Though the use amount of the solvent is not restricted, it is usually 100 parts by weight or less with respect to 1 part by weight of benzal halide compound (5) from the standpoint of volumetric efficiency.

The reaction of benzal halide compound (5) with phenol compound (6) is preferably carried out in the presence of a phase transfer catalyst.

The phase transfer catalyst includes quaternary ammonium salts such as tetra n-butylammonium bromide, benzyltriethylammonium chloride, tetra n-butylammonium hydrogen sulfate, trioctylmethylammonium chloride and the like; phosphonium salts such as triphenylphosphine bromide and the like; polyether compounds such as 18-crown-6, polyethylene glycol; and quaternary ammonium salts are preferable, and tetra n-butylammonium bromide is more preferable.

The use amount of the phase transfer catalyst is usually 0.01 mol or more, preferably 0.05 to 1 mol with respect to 1 mol of the compound which is used in the smaller amount of benzal halide compound (5) and phenol compound (6).

By carrying out a reaction of benzal halide compound (5) with phenol compound (6) in the presence of iodine or an iodine compound, the reaction can be progressed more smoothly.

The iodine compound includes alkali metal iodides such as potassium iodide, sodium iodide and lithium iodide. Alkali metal iodides are preferable and potassium iodide is more preferable. As iodine or an iodine compound, commercially available compounds are usually used as they are.

The use amount of iodine or an iodine compound is usually 0.01 mol or more, preferably 0.05 to 1 mol with respect to 1 mol of the compound which is used in the smaller amount of benzal halide compound (5) and phenol compound (6).

The reaction temperature is usually −5° C. or more and not higher than the boiling point of a solvent, and preferably 10 to 100° C.

The reaction may be carried out at normal pressure, or carried out under increased pressure.

The reaction is carried out by mixing benzal halide compound (5), phenol compound (6) and a base. The mixing order thereof is not restricted, and benzal halide compound (5), phenol compound (6) and a base may be added into a reaction vessel simultaneously, or a base may be added to a mixture of benzal halide compound (5) and phenol compound (6). Phenol compound (6) may be added to a mixture of benzal halide compound (5) and a base, or a mixture of phenol compound (6) and a base may be added to benzal halide compound (5). Among them, the method of adding a mixture of phenol compound (6) with a base to benzal halide compound (5) is preferable.

The progress of the reaction can be confirmed by usual analysis means such as gas chromatography, high performance liquid chromatography and NMR.

Thus, a reaction mixture containing benzal halide compound (1) is obtained, and benzal halide compound (1) can be separated out by, for example, washing the reaction mixture with an aqueous solution of an acid if necessary, and then performing concentration thereof. The benzal halide compound (1) separated out may be further purified by usual purification means such as recrystallization, distillation and column chromatography. Further, the resultant reaction mixture may be used as it is for the above-described reaction with an alkali metal alkoxide (2).

EXAMPLES

The present invention will be illustrated further in detail by examples below, but the present invention is not limited to these examples. Analysis was carried out by a high performance liquid chromatography internal standard method.

Example 1

Into a 500 mL round-bottomed flask was added 50.2 g of 2,5-dimethylphenol and 100 mL of toluene. Onto the resultant mixture, 171.6 g of a 10 wt % sodium hydroxide aqueous solution was dropped at room temperature. The resultant mixture was stirred at 80° C. for 1 hour, then, cooled down to 40° C., to prepare Mixture A Into another 500 mL round-bottomed flask was added 76.4 g of 2-(chloromethyl)benzal chloride (content: 98.0 wt %), 5.8 g of tetra n-butylammonium bromide and 75 mL of toluene. Onto the resultant mixture, an aqueous layer of Mixture A prepared above was dropped at 40° C. over a period of 6 hours, and subsequently, an oil layer of Mixture A was dropped over a period of 0.5 hours. After completion of dropping, the resultant mixture was stirred at the same temperature for 4 hours.

The resultant reaction mixture was cooled down to room temperature, and to this was added 4.0 g of a 20 wt % sulfuric acid aqueous solution. The resultant mixture was separated, and the resultant organic layer was washed with 153.0 g of water. The resultant organic layer was concentrated under reduced pressure to give 110.9 g of crude 2-(2,5-dimethylphenoxymethyl)benzal chloride as yellow-brown solid. Content: 87.2 wt % Yield: 91.7% (based on 2-(chloromethyl)benzal chloride)

$^1$H-NMR (CDCl$_3$) δ ppm: 2.25 (3H, s), 2.38 (3H, s), 5.20 (2H, s), 6.76-6.81 (2H, m), 7.09 (1H, d, J=7.41 Hz), 7.18 (1H, s), 7.41-7.54 (3H, m), 7.97 (1H, d, J=7.69 Hz)

Melting point: 62-65° C.

Example 2

Into a 200 mL round-bottomed flask was added 32.8 g of 2,5-dimethylphenol and 57 mL of xylene. Onto the resultant mixture, 51.3 g of a 20 wt % sodium hydroxide aqueous solution was dropped at room temperature. The resultant mixture was stirred at 80° C. for 1 hour, then, cooled down to 40° C., to prepare Mixture B.

Into another 500 mL round-bottomed flask was added 50.0 g of 2-(chloromethyl)benzal chloride (content: 98.0 wt %), 3.8 g of tetra n-butylammonium bromide and 57 mL of xylene. Onto the resultant mixture, an aqueous layer of Mixture B prepared above was dropped at 40° C. over a period of 6 hours, and subsequently, an oil layer of Mixture B was dropped over a period of 0.5 hours. After completion of dropping, the resultant mixture was stirred at the same temperature for 4 hours.

The resultant reaction mixture was cooled down to room temperature, and to this was added 2.8 g of a 20 wt % sulfuric acid aqueous solution. The resultant mixture was separated, and the resultant organic layer was washed with 100.0 g of water. The resultant organic layer was concentrated under reduced pressure to give 73.5 g of crude 2-(2,5-dimethylphenoxymethyl)benzal chloride as yellow-brown solid. Content: 85.5 wt % Yield: 91.0% (based on 2-(chloromethyl)benzal chloride)

Example 3

Into a 200 mL round-bottomed flask was added 19.1 g of 2,5-dimethylphenol and 30 mL of toluene. Onto the resultant mixture, 65.5 g of a 10 wt % sodium hydroxide aqueous solution was dropped at room temperature. The resultant mixture was stirred at 80° C. for 1 hour, then, cooled down to 40° C., to give Mixture C.

Into another 500 mL round-bottomed flask was added 30.0 g of 2-(chloromethyl)benzal chloride (content: 98.0 wt %), 1.6 g of benzyltriethylammonium chloride and 30 mL of toluene. Onto the resultant mixture, an aqueous layer of Mixture C prepared above was dropped at 40° C. over a period 6 hours, and subsequently, an oil layer of Mixture C was dropped over a period of 0.5 hours. After completion of dropping, the resultant mixture was stirred at the same temperature for 4 hours.

The resultant reaction mixture was cooled down to room temperature, and to this was added 1.7 g of a 20 wt % sulfuric acid aqueous solution. The resultant mixture was separated, and the resultant organic layer was washed with 60.0 g of water. The resultant organic layer was concentrated under reduced pressure, to give 39.7 g of crude 2-(2,5-dimethylphenoxymethyl)benzal chloride as yellow-brown solid. Content: 75.1 wt % Yield: 72.1% (based on 2-(chloromethyl)benzal chloride)

Example 4

Into a 100 mL round-bottomed flask was added 6.35 g of 2,5-dimethylphenol, 7.66 g of potassium carbonate, 0.4 g of potassium iodide and 30 mL of acetonitrile. Onto the resultant mixture, 10.0 g of 2-(chloromethyl)benzal chloride (content: 98.0 wt %) was dropped at room temperature. After completion of dropping, the resultant mixture was stirred at 80° C. for 30 hours.

The resultant reaction mixture was cooled down to room temperature, and to this was added 50 g of water and 100 g of toluene. The resultant mixture was separated, and the resultant organic layer was washed with 20.0 g of water. The resultant organic layer was concentrated under reduced pressure, to give 15.3 g of crude 2-(2,5-dimethylphenoxymethyl)benzal chloride as yellow-brown solid. Content: 77.5 wt % Yield: 85.8% (based on 2-(chloromethyl)benzal chloride)

Example 5

Into a 500 mL round-bottomed flask was added 188 mL of methanol and 75.1 g of 2-(2,5-dimethylphenoxymethyl)benzal chloride (content: 99.0 wt %). The resultant solution was heated, and the internal temperature was adjusted to 85° C. while discharging a part of methanol. Onto the solution, 242.9 g of a 28 wt % sodium methoxide/methanol solution was dropped at an internal temperature of 80 to 85° C. over a period of 7 hours. During dropping, the internal temperature was maintained in the range of 80 to 85° C. by discharging apart of methanol from the reaction mixture. After completion of dropping, the resultant mixture was stirred at the same temperature for 16 hours.

The resultant reaction mixture was cooled down to an internal temperature of 60° C., and 22 mL of xylene and 225 mL of water were added. The resultant mixture was separated, and to the resultant organic layer was added 150.0 g of a 35 wt % sulfuric acid aqueous solution. The resultant mixture was stirred at 60° C. for 2 hours, and 187 mL of xylene was added. The resultant mixture separated at the same temperature, and the resultant organic layer was cooled down to room temperature. The organic layer was washed with 75.0 g of a 5 wt % sodium hydroxide aqueous solution, then, with 150 mL of water. The resultant organic layer was concentrated under reduced pressure, to give 61.1 g of crude 2-(2,5-dimethylphenoxymethyl)benzaldehyde as yellow solid. Content: 97.2 wt % Yield: 98.1% (based on 2-(2,5-dimethylphenoxymethyl)benzal chloride)

Example 6

Into a 500 mL round-bottomed flask was added 20.0 g of 2-(2,5-dimethylphenoxymethyl)benzal chloride (content: 95.0 wt %). Onto this, 37.3 g of a 28 wt % sodium methoxide/methanol solution was dropped at an internal temperature of 80 to 85° C. over a period of 7 hours. During dropping, the internal temperature of was maintained in the range of 80 to 85° C. by discharging apart of methanol. After completion of dropping, the resultant mixture was stirred at the same temperature for 40 hours.

The resultant reaction mixture was cooled down to an internal temperature of 60° C., and to this was added 7 mL of xylene and 40 mL of water. The resultant mixture was separated, and to the resultant organic layer was added 40.0 g of a 35 wt % sulfuric acid aqueous solution. The resultant mixture was stirred at 60° C. for 2 hours, and 23 mL of xylene was added. The resultant mixture was separated at the same temperature, and the resultant organic layer was cooled down to room temperature. The organic layer was washed with 20.0 g of a 5 wt % sodium hydroxide aqueous solution, then, with 40.0 g of water. The resultant organic layer was concentrated under reduced pressure, to give 16.2 g of crude 2-(2,5-dimethylphenoxymethyl)benzaldehyde as yellow solid. Content: 94.5 wt % Yield: 99.0% (based on 2-(2,5-dimethylphenoxymethyl)benzal chloride)

Example 7

Into a 30 mL round-bottomed flask was added 2.0 g of 2-(2,5-dimethylphenoxymethyl)benzal chloride (content: 95.0 wt %) and 0.05 g of potassium iodide. Onto the resultant mixture, 3.25 g of a 28 wt % sodium methoxide/methanol solution was dropped at an internal temperature of 80 to 85° C. over a period of 7 hours. During dropping, the internal temperature was maintained in the range of 80 to 85° C. by discharging a part of methanol from the reaction mixture. After completion of dropping, the resultant mixture was stirred at the same temperature for 16 hours.

The resultant reaction mixture was cooled down to an internal temperature of 60° C., and to this was added 1 mL of xylene and 10 mL of water. The resultant mixture was separated, and to the resultant organic layer was added 4.0 g of a 35 wt % sulfuric acid aqueous solution. The resultant mixture was stirred at 60° C. for 2 hours, and 10 mL of xylene was added. The resultant mixture was separated at the same temperature, and the resultant organic layer was cooled down to room temperature. The organic layer was washed with 2.0 g of a 5 wt % sodium hydroxide aqueous solution, then, with 4.0 g of water. The resultant organic layer was concentrated under reduced pressure, to give 1.58 g of crude 2-(2,5-dimethylphenoxymethyl)benzaldehyde as yellow solid. Content: 94.6 wt % Yield: 97.1% (based on 2-(2,5-dimethylphenoxymethyl)benzal chloride)

Example 8

Into a 50 mL round-bottomed flask was added 5.0 g of 2-(2,5-dimethylphenoxymethyl)benzal chloride (content: 85.0 wt %) and 0.23 g of tetrabutylammonium bromide. Onto the resultant mixture, 8.33 g of a 28 wt % sodium methoxide/methanol solution was dropped at an internal temperature of 80 to 85° C. over a period of 7 hours. During dropping, the internal temperature was maintained in the range of 80 to 85° C. by discharging a part of methanol from the reaction mixture. After completion of dropping, the resultant mixture was stirred at the same temperature for 25 hours.

The resultant reaction mixture was cooled down to an internal temperature of 60° C., and to this was added 3 mL of xylene and 25 mL of water. The resultant mixture was separated, and to the resultant organic layer was added 10.0 g of a 35 wt % sulfuric acid aqueous solution. The resultant mixture was stirred at 60° C. for 2 hours, and 22 mL of xylene was added. The resultant mixture was separated at the same temperature, and the resultant organic layer was cooled down to room temperature. The organic layer was washed with 5.0 g of a 5 wt % sodium hydroxide aqueous solution, then, with 10.0 g of water. The resultant organic layer was concentrated under reduced pressure, to give 4.01 g of crude 2-(2,5-dimethylphenoxymethyl)benzaldehyde as yellow solid. Content: 84.0 wt % Yield: 97.3% (based on 2-(2,5-dimethylphenoxymethyl)benzal chloride)

Example 9

Into a 500 mL round-bottomed flask was added 75.0 g of 2-(2,5-dimethylphenoxymethyl)benzal chloride (content: 99.0 wt %) and 188 mL of methanol. The resultant solution was heated, and the internal temperature was adjusted to 85° C. while discharging a part of methanol. Onto the solution, 242.9 g of a 28 wt % sodium methoxide/methanol solution was dropped at an internal temperature of 80 to 85° C. over a period of 7 hours. During dropping, the internal temperature was maintained in the range of 80 to 85° C. by discharging a part of methanol from the reaction mixture. After completion of dropping, the resultant mixture was stirred at the same temperature for 16 hours.

The resultant reaction mixture was cooled down to room temperature, and to this was added 78 mL of xylene and 225 mL of water. The resultant mixture was separated, and the resultant organic layer was concentrated under reduced pressure, to give 73.7 g of crude 2-(2,5-dimethylphenoxymethyl)benzaldehyde dimethyl acetal as yellow oil. Content: 96.3 wt % Yield: 99.1% (based on 2-(2,5-dimethylphenoxymethyl)benzal chloride)

$^1$H-NMR (CDCl$_3$) δ ppm: 2.28 (3H, s), 2.36 (3H, s), 3.38 (6H, s), 5.22 (2H, s), 5.60 (1H, s), 6.73 (1H, d, J=7.53 Hz), 6.78 (1H, s), 7.07 (1H, d, J=7.43 Hz), 7.35-7.44 (2H, m), 7.63 (1H, s), 7.64 (1H, d, J=7.29 Hz)

Example 10

The crude 2-(2,5-dimethylphenoxymethyl)benzaldehyde dimethyl acetal (73.7 g) obtained in Example 9, 22 mL of xylene and 150.0 g of a 35 wt % sulfuric acid aqueous solution were mixed. The resultant mixture was stirred at 60° C. for 2 hours. To this was added 187 mL of xylene, and the resultant mixture was separated at the same temperature. The resultant organic layer was cooled down to room temperature, then, washed with 75.0 g of a 5 wt % sodium hydroxide aqueous solution, then, with 150 mL of water. The resultant organic layer was concentrated under reduced pressure, to give 60.5 g of crude 2-(2,5-dimethylphenoxymethyl)benzaldehyde as yellow solid. Content: 97.1 wt % Yield: 97.1% (based on 2-(2,5-dimethylphenoxymethyl)benzal chloride)

INDUSTRIAL APPLICABILITY

A benzaldehyde compound which is useful as a production intermediate of a disinfectant can be produced with good yield, by reacting a benzaldehyde acetal compound which is a novel compound of the present invention, and water, in the presence of an acid.

The invention claimed is:

1. A benzaldehyde acetal compound of formula (3):

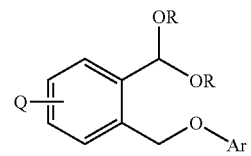

(3)

(wherein Q represents a hydrogen atom or a halogen atom, Ar represents a phenyl group optionally substituted with at least one selected from the group consisting of alkyl groups having 1 to 4 carbon atoms and halogen atoms, and R represents an alkyl group having 1 to 4 carbon atoms).

2. The benzaldehyde acetal compound according to claim 1, wherein R is a methyl group.

3. The benzaldehyde acetal compound according to claim 1, wherein Ar is a phenyl group substituted with at least one alkyl group having 1 to 4 carbon atoms.

4. The benzaldehyde acetal compound according to claim 3, wherein the phenyl group substituted with at least one alkyl group having 1 to 4 carbon atoms is 2,5-dimethylphenyl group.

5. The benzaldehyde acetal compound according to claim 1, wherein R is a methyl group, Ar is 2,5-dimethylphenyl group and Q is a hydrogen atom.

6. A method for producing a benzaldehyde compound of formula (4):

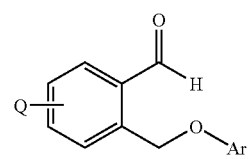

(4)

(wherein Q and Ar respectively represent the same meanings as described below), which comprises reacting a benzaldehyde acetal compound of formula (3):

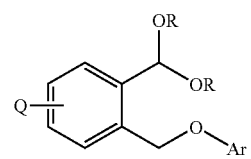

(3)

(wherein Q represents a hydrogen atom or a halogen atom, Ar represents a phenyl group optionally substituted with at least one selected from the group consisting of alkyl groups having 1 to 4 carbon atoms and halogen atoms, and R represents an alkyl group having 1 to 4 carbon atoms) with water in the presence of an acid.

7. The method for producing a benzaldehyde compound according to claim 6, wherein the acid is a Broensted acid.

8. The method for producing a benzaldehyde compound according to claim 7, wherein the Broensted acid is sulfuric acid.

9. A method for producing a benzaldehyde dialkylacetal compound of formula (3):

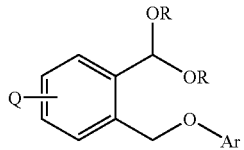
(3)

(wherein Q, Ar and R respectively represent the same meanings as described below) which comprises reacting a benzal halide compound of formula (1):

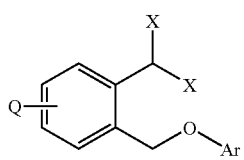
(1)

(wherein Q represents a hydrogen atom or a halogen atom, X represents a halogen atom and Ar represents a phenyl group optionally substituted with at least one selected from the group consisting of alkyl groups having 1 to 4 carbon atoms and halogen atoms) with an alkali metal alkoxide of formula (2):

RO—M    (2)

(wherein R represents an alkyl group having 1 to 4 carbon atoms and M represents an alkali metal atom).

10. The method for producing a benzaldehyde dialkylacetal compound according to claim 9, wherein the benzal halide compound of formula (1) and the alkali metal alkoxide of formula (2) are reacted in the presence of iodine or an iodine compound.

11. The method for producing a benzaldehyde dialkylacetal compound according to claim 10, wherein the iodine compound is an alkali metal iodide.

12. The method for producing a benzaldehyde dialkylacetal compound according to claim 9, wherein the benzal halide compound of formula (1) and the alkali metal alkoxide of formula (2) are reacted in the presence of a phase transfer catalyst.

13. The method for producing a benzaldehyde dialkylacetal compound according to claim 12, wherein the phase transfer catalyst is a quaternary ammonium salt.

14. A benzal halide compound of formula (1):

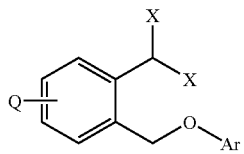
(1)

(wherein Q represents a hydrogen atom or a halogen atom, X represents a halogen atom and Ar represents a phenyl group optionally substituted with at least one selected from the group consisting of alkyl groups having 1 to 4 carbon atoms and halogen atoms).

15. The benzal halide compound according to claim 14, wherein the halogen atom is a chlorine atom.

16. The benzal halide compound according to claim 14, wherein Ar is a phenyl group substituted with at least one alkyl group having 1 to 4 carbon atoms.

17. The benzal halide compound according to claim 16, wherein the phenyl group substituted with at least one alkyl group having 1 to 4 carbon atoms is 2,5-dimethylphenyl group.

18. The benzal halide compound according to claim 14, wherein X is a chlorine atom, Ar is 2,5-dimethylphenyl group and Q is a hydrogen atom.

19. A method for producing a benzal halide compound of formula (1):

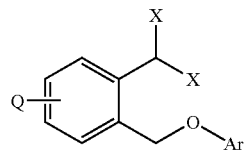
(1)

(wherein Q, X and Ar respectively represent the same meanings as described below),
which comprises reacting a benzal halide compound of formula (5):

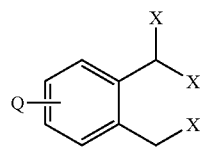
(5)

(wherein Q and X respectively represent the same meanings as described above) with a phenol compound of formula (6):

Ar—OH    (6)

(wherein Ar represents the same meaning as described above) in the presence of a base.

20. The method for producing a benzal halide compound according to claim 19, wherein a mixture of the phenol compound of formula (6) with a base is added to the benzal halide compound of formula (5) to perform a reaction thereof.

21. The method for producing a benzal halide compound according to claim 19, wherein the benzal halide compound of formula (5) and the phenol compound of formula (6) are reacted in the presence of a phase transfer catalyst.

22. A method for producing a benzaldehyde compound, which comprises
(A) a step of reacting a benzal halide compound of formula (1):

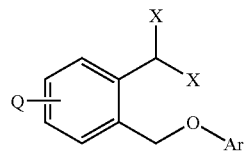
(1)

(wherein Q represents a hydrogen atom or a halogen atom, X represents a halogen atom and Ar represents a phenyl group optionally substituted with at least one selected from the group consisting of alkyl groups having 1 to 4 carbon atoms and halogen atoms) with an alkali metal alkoxide of formula (2):

 (2)

(wherein R represents an alkyl group having 1 to 4 carbon atoms and M represents an alkali metal atom)
to give a benzaldehyde dialkylacetal compound of formula (3):

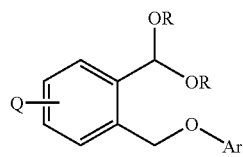 (3)

(wherein Q, Ar and R respectively represent the same meanings as described above), and
(B) a step of reacting the benzaldehyde dialkylacetal compound of formula (3) with water in the presence of an acid to give a benzaldehyde compound of formula (4):

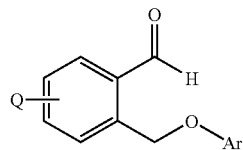 (4)

(wherein Q and Ar respectively represent the same meanings as described above).

23. The method for producing a benzaldehyde compound according to claim 22, further comprising
(C) a step of reacting a benzal halide compound of formula (5):

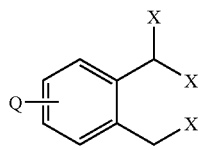 (5)

(wherein Q and X respectively represent the same meanings as described above) with a phenol compound of formula (6):

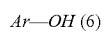 (6)

(wherein Ar respectively represents the same meaning as described above) in the presence of a base to give the benzal halide compound of formula (1):

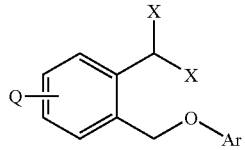 (1)

(wherein Q, X and Ar respectively represent the same meanings as described above).

* * * * *